Figure 1:
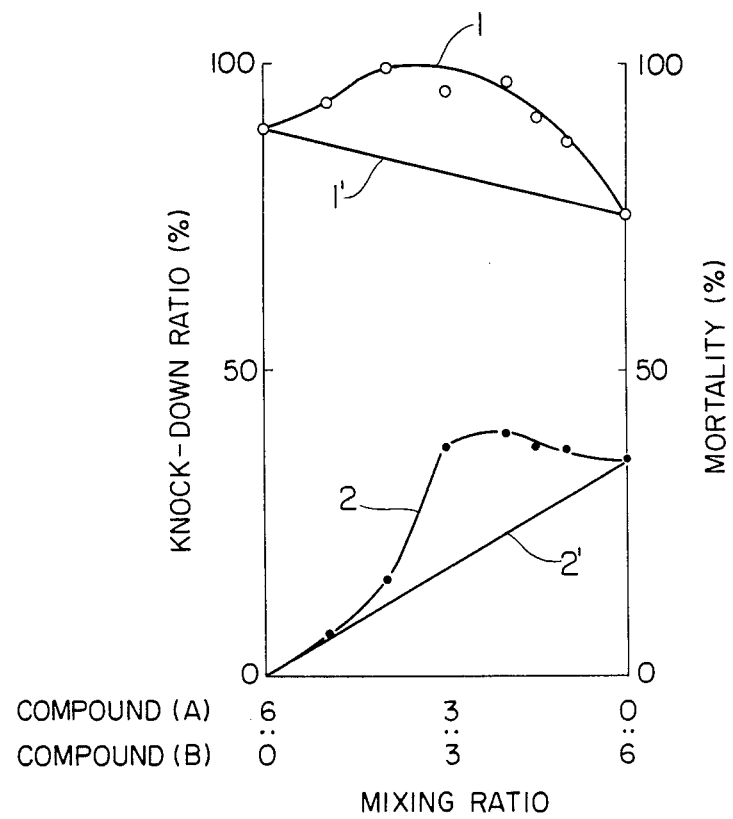

United States Patent [19]

Shinjo et al.

[11] Patent Number: 4,562,062
[45] Date of Patent: Dec. 31, 1985

[54] INSECTICIDAL COMPOSITION COMPRISING SYNERGISTIC COMBINATIONS OF 3-(2-METHOXYPHENYL)-5-METHOXY-1,3,4-OXADIAZOL-2(3H)-ONE AND PYRETHROID TYPE COMPOUNDS

[75] Inventors: Goro Shinjo, Toyonaka; Mitsuyasu Makita, Nishinomiya; Shigenori Tsuda, Toyonaka, all of Japan

[73] Assignee: Sumitomo Chemical Company, Limited, Osaka, Japan

[21] Appl. No.: 617,031

[22] Filed: Jun. 4, 1984

[30] Foreign Application Priority Data

Jun. 10, 1983 [JP] Japan .................... 58-104533

[51] Int. Cl.$^4$ .................... A01N 43/82; A61L 9/04
[52] U.S. Cl. .................... 424/45; 514/364
[58] Field of Search .................... 424/272, 45; 514/364

[56] References Cited

U.S. PATENT DOCUMENTS 3,899,586  8/1975  Okuno et al. .................... 424/40
4,150,142  4/1979  Boesch .................... 424/272
4,308,262  12/1981  Badmin et al. .................... 424/260

OTHER PUBLICATIONS

"Insecticides And Actual Prevention And Removal Of Harmful Insects", pp. 68–76, Published Apr. 1, 1983.
Central Patents Indes, Basic Abstracts Journal Section C, AGDOC Week E44, Jan. 5,1983, Abstract 93488 E/44, London, GB & JP-A-82 154 108 (Mitsubishi).
Central Patents Index, Basic Abstracts Journal Section C, AGDOC Week K12, May 16, 1983, Abstract 28605 K/12, London, GB; & JP-A-83 024 505 (Mitsubishi).

*Primary Examiner*—Allen J. Robinson
*Attorney, Agent, or Firm*—Stevens, Davis, Miller & Mosher

[57] ABSTRACT

An insecticidal composition characterized in that said composition contains 3-(2-methoxyphenyl)-5-methoxy-1,3,4-oxadiazol-2(3H)-one and at least one of the pyrethroid type compounds represented by the formula,

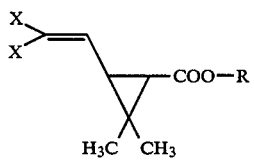

which has a remarkable synergistic action in both the rapid knock-down effect and high lethal effect.

3 Claims, 3 Drawing Figures

INSECTICIDAL COMPOSITION COMPRISING SYNERGISTIC COMBINATIONS OF 3-(2-METHOXYPHENYL)-5-METHOXY-1,3,4-OXADIAZOL-2(3H)-ONE AND PYRETHROID TYPE COMPOUNDS

The present invention relates to an insecticidal composition, and more particularly, it relates to an insecticidal composition characterized in that said composition contains 3-(2-methoxyphenyl)-5-methoxy-1,3,4-oxadiazol-2(3H)-one [hereinafter referred to as compound (A)] and at least one of the pyrethroid type compounds represented by the formula (I),

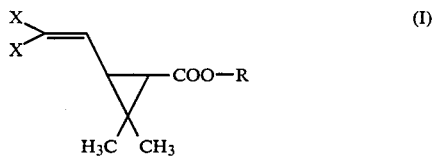

wherein X represents a methyl group or chlorine atom, and R represents a group selected from the group consisting of the formulae,

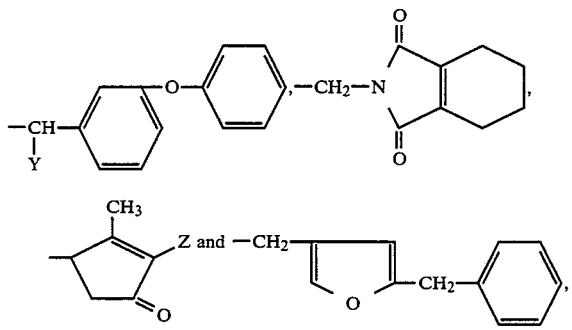

in which Y is a hydrogen atom or a cyano group, Z is a 2-propenyl or 2-propynyl group, in a weight ratio of oxadiazol compound to pyrethroid compound being from 10:1 to 1:5.

As a result of an extensive study to search for higher performance insecticides which are of lower toxicity as well as more rapid insecticidal effect, the present inventors found that the composition described above has a remarkable synergistic action in both the rapid knockdown effect and high lethal effect, and confirmed that said composition is particularly superior in an effect on cockroaches of which control is strongly demanded in recent years. The present inventors thus completed the present invention. The present invention will be illustrated in detail hereinafter.

In the present invention, as the pyrethroid type compound represented by the foregoing formula (I), there are given permethrins (permethrin and its optical and/or geometrical isomers), cypermethrins (cypermethrin and its optical and/or geometrical isomers), cyphenothrins (cyphenothrin and its optical and/or geometrical isomers), phenothrins (phenothrin and its optical and/or geometrical isomers), tetramethrins (tetramethrin and its optical and/or geometrical isomers), allethrins (allethrin and its optical and/or geometrical isomers), prallethrins (dl-2-propargyl-3-methyl-cyclopent-2-en-1-one dl-cis/trans-chrysanthemate and its optical and/or geometrical isomers), resmethrins (resmethrin and its optical and/or geometrical isomers).

In the insecticidal composition of the present invention, the content ratio (by weight) of these pyrethroid type compounds to the compound (A) is 0.1-5:1.

Also, in applying this composition to practical uses, it is formulated, according to the common insecticide-preparation methods well known to those skilled in the art, into various preparation forms such as emulsifiable concentrates, wettable powders, dusts, oil liquid, aerosols, fumigants (e.g. mosquito coils, mosquito mats for electric fumigators), foggings and the like by mixing with a solid, liquid or gaseous carrier of other auxiliaries for formulation (e.g. surface active agents, dispersing agents, wetting agents, stabilizers).

In these preparation methods, as the solid carrier, there are given for example fine powders or granules of clays (e.g. kaolin, bentonite, terra abla, pyrophyllite, sericite), talcs, other inorganic minerals (e.g. hydrated silicon dioxide, pumice, diatomaceous earth, sulfur powder, activated carbon) and the like.

As the liquid carrier, there are given for example alcohols (e.g. methyl alcohol), ketones (e.g. acetone, methyl ethyl ketone), ethers (e.g. ethyl ether, dioxane, cellosolve, tetrahydrofuran), aromatic hydrocarbons (e.g. benzene, toluene, xylene, methylnaphthalene), aliphatic hydrocarbons (e.g. kerosene), esters, nitriles, acid amides (e.g. dimethylformamide, dimethyl acetamide), halogenated hydrocarbons (e.g. dichloroethane, trichloroethylene, carbon tetrachloride) and the like.

As the surface active agent, there are given for example alkyl sulfates, alkylsulfonates, alkylarylsulfonates, polyethylene glycol ethers, polyhydric alcohol esters and the like.

Further, the usable fixing agent and dispersing agent include for example casein, gelatin, starch powder, CMC, sodium-CMC, gum arabic, alginic acid, lignosulfonates, bentonite, molasses, polyvinyl alcohol, pine oil, agar and the like. As the stabilizer, there are given for example PAP (isopropyl phosphate), TCP (tricresyl phosphate), tall oil, epoxidized oil, various surface active agents, various fatty acids or their esters, and the like.

As described above, the insecticidal composition of the present invention is particularly suitable for the control of cockroaches so that, in using it for such purpose, its insecticidal effect can be developed more efficiently by using it in the form of a fumigant, aerosol and oil liquid. In particular, the fumigant containing cypermethrins, permethrins or cyphenothrins as the pyrethroid type compound, and the aerosol containing cypermethrins, permethrins, cyphenothrins or tetramethrins as the pyrethroid type compound are more preferable.

As the form of such fumigant, there may be given for example types suitable for burning (e.g. "jet" type formulations, "rod" type formulations), exothermic reaction (e.g. types generating heat by water addition or air oxidation), electric heating (e.g. mat) and the like.

As a main base for the "jet" type formulations, there are given for example, mixtures of a nitrate or nitrite and a thermal decomposition-stimulating agent (e.g. salts of an alkaline earth metal or alkali metal), mixtures of a guanidine salt and a thermal decomposition-stimulating agent (e.g. bichromates, chromates), and the like.

As a main base for the "rod" type formulations, there are given for example, mixtures of a burning agent (e.g.

ethyl cellulose, nitrocellulose), a flame-extinguishing agent (e.g. melamine, flour), a filler (e.g. diatomaceous earth) and a vehicle and the like. This mixture is kneaded and then formed into a rod.

As a main base for the type which generates heat by air oxidation, there are given for example, mixtures of a heat-generating agent (e.g. sulfides, polysulfides or hydrosulfides of an alkali metal, their hydrated salts), a catalytic substance (e.g. carbon black, activated carbon, charcoal, coke, asphalt) and a filler (e.g. natural fibers, synthetic fibers, synthetic resin foams), and the like.

As a main base for the type which generates heat by water addition, there are given for example, mixtures of an organic foaming agent (e.g. azodicarbonamide, benzene-sulfonyl hydrazide) and a heat-generating agent (e.g. calcium oxide), and the like.

As the mat, there may be given for example, mats produced by impregnating the porous plate of asbestos, pulp, ceramics, etc with an active ingredient dissolved in an organic solvent such as acetone. And as the aerosol, there may be given for example, aerosol containing the organic solvent such as methylene chloride, kerosene or the like as the liquid carrier and being charged with propellant such as liquid petroleum gas.

As the oil liquid, there may be given for example, the oil liquid containing the organic solvent such as methylene chloride, kerosene or the like.

The foregoing composition contains 0.5 to 40% by weight, generally 1 to 30% by weight, of the active ingredients.

Next, the present invention will be illustrated in more detail with reference to the following examples, but it is not to be interpreted as being limited thereto.

The attached FIG. 1 shows a diagram illustrating the test result on 10 minutes' exposure among the test results described in the following Table 1 which were obtained in the following Experimental example 1. In the figure, a curve ① shows the found value of a mortality, a curve ①' the theoretical value of the same, a curve ② the found value of a knock-down ratio and a curve ②' the theoretical value of the same. The abscissa indicates the mixing ratio of compound (A) to compound (B), the left ordinate indicates the knock-down ratio (%) and the right ordinate indicates the mortality (%).

Figure 2:
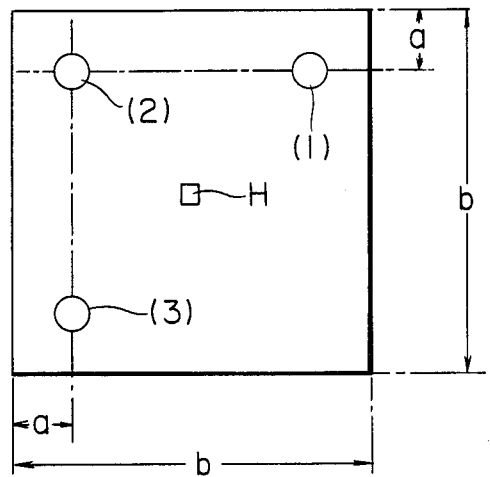
Figure 3:
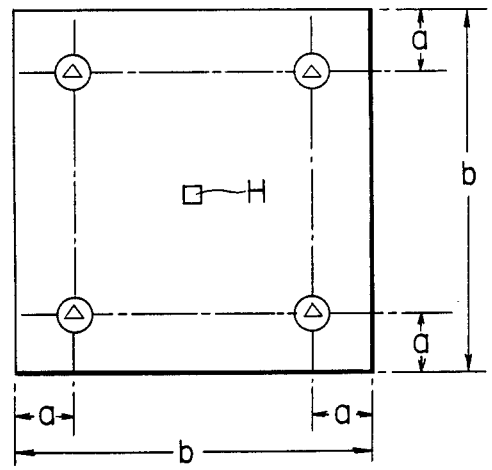

The attached FIG. 2 shows the positions in the Peet Grady's chamber in the following Experimental Example 2 at which the test plots (1), (2) and (3) were placed. The attached FIG. 3 shows the positions in the Peet Grady's chamber in the following Experimental Example 3 at which the triangular shelters were placed. In FIGS. 2 and 3, H indicates the position of the electro-heating type fumigant or mat, and distances, a and b, are 30 cm and 180 cm, respectively.

In the following examples, the symbol of the pyrethroid type compounds are as shown below and the parts are by weight.

| Symbol | Name |
| --- | --- |
| (B) | permethrin |
| (C) | cypermethrin |
| (D) | d-cyphenothrin |
| | (α-cyano-3-phenoxybenzyl d-cis/trans-chrysanthemate) |
| (E) | d-phenothrin |
| | (3-phenoxybenzyl d-cis/trans-chrysanthemate) |
| (F) | tetramethrin |
| (G) | d-tetramethrin |
| | (3,4,5,6-tetrahydrophthalimidomethyl d-cis/trans-chrysanthemate) |
| (H) | d-allethrin |
| | (allethronyl d-cis/trans-chrysanthemate) |
| (I) | bio-allethrin |
| | (allethronyl d-trans-chrysanthemate) |
| (J) | (S)bioallethrin |
| | (d-allethronyl d-trans-chrysanthemate) |
| (K) | Esbiothrin |
| | (the mixture of bio-allethrin and (S)bioallethrin) |
| (L) | resmethrin |
| (M) | d-resmethrin |
| | (5-benzyl-3-furylmethyl d-cis/trans-chrysanthemate) |
| (N) | bio-resmethrin |
| | (5-benzyl-3-furylmethyl d-trans-chrysanthemate) |

FORMULATION EXAMPLE 1

By admixing the active ingredients, nitrocellulose, malamine, sodium-CMC and diatomaceus earth at the mixing ratios as given in Table below, the "rod" type formulations for fumigation in each case are prepared.

| | Composition of "rod" type formulations | | | | | |
| --- | --- | --- | --- | --- | --- | --- |
| | Active ingredients | | | | | Diatomaceus earth |
| No. | Compound (A) | Pyrethroid type compound | Nitro-cellulose | Melamine | Sodium-CMC | |
| 1 | 1 part | (B): 1 part | 35 parts | 20 parts | 4 parts | 39 parts |
| 2 | 18 parts | (C): 2 parts | " | " | " | 21 parts |
| 3 | 2 parts | (D): 10 parts | " | " | " | 29 parts |
| 4 | 9 parts | (E): 21 parts | 40 parts | " | " | 6 parts |
| 5 | 0.2 part | (C): 0.8 part | " | " | " | 35 parts |
| 6 | 6 parts | (B): 4 parts | " | " | " | 26 parts |
| 7 | " | (D): 4 parts | " | " | " | " |

FORMULATION EXAMPLE 2

The mixture of the active ingredients and the Yoshinox 424 [2,2'-methylenebis(4-ethyl-6-tert-butyl-phenol); stabilizer (manufactured by Yoshitomi Pharmaceutical Industries, Ltd.)] at the mixing ratio as given in Table below was dissolved in 5 ml of acetone. And the solution was adsorbed uniformly on the porous ceramic plate [4 cm × 4 cm × 1.2 cm (thickness)] having a weight of 10 g to prepare an insecticidal mat for heating fumigation.

| | Formulation of Mat for heating fumigation | | |
| --- | --- | --- | --- |
| | Active ingredients | | |
| No. | Compound (A) | Pyrethroid type compound | Yoshinox 424 |
| 1 | 200 mg | (C): 300 mg | 100 mg |
| 2 | 500 mg | (C): 1000 mg | 300 mg |
| 3 | 1200 mg | (B): 800 mg | 600 mg |
| 4 | 500 mg | (K): 2000 mg | 300 mg |

-continued

| Formulation of Mat for heating fumigation | | | |
|---|---|---|---|
| | Active ingredients | | |
| No. | Compound (A) | Pyrethroid type compound | Yoshinox 424 |
| 5 | 1000 mg | (D): 800 mg | 500 mg |

FORMULATION EXAMPLE 3

A mixture of one part of the compound (A) and 0.1 part of compound (B), (C), (D), (E), (F), (G), (H), (I), (J), (K), (L), (M) or (N) is dissolved in 20 parts of methylene chloride and made up to 60 parts of solution with deodorized kerosene.

The solution is filled in an aerosol container. After attaching a valve portion to the container, 40 parts of a propellant (liquid petroleum gas) is charged therein under pressure through the valve to obtain the aerosol.

FORMULATION EXAMPLE 4

A mixture of 0.5 part of compound (A) and 0.1 part of compound (F), (G), (H) or (K) is dissolved in 16 parts of methylene chloride and made up to 100 parts with kerosene to obtain the oil liquid.

FORMULATION EXAMPLE 5

A mixture of 5 parts of the compound (A) and 5 parts of the compound (B), (C), (D) or (E) is dissolved in 55 parts of methylene chloride.

The solution is filled in an aerosol container. After attaching a valve portion to the container, 35 parts of a propellant (liquid petroleum gas) is charged therein under pressure through the valve to obtain the aerosol.

FORMULATION EXAMPLE 6

A mixture of one part of compound (A) and 0.1 part of compound (F), (G), (H) or (M) is dissolved in 20 parts of methylene chloride and made up to 100 parts with kerosene to obtain the oil liquid.

FORMULATION EXAMPLE 7

A mixture of one part of compound (A) and one part of compound of (B), (C), (D) or (E) is dissolved in 20 parts of methylene chloride and made up to 100 parts with kerosene to obtain the oil liquid.

EXPERIMENTAL EXAMPLE 1

"Rod" type formulations for fumigation having a composition shown in Tables 1 and 2, were prepared according to the following preparation method.

A rod-form base was prepared by mixing 35% of nitrocellulose and a mixture of a flame-extinguishing agent, a diluent and diatomaceous earth so that the total was 100%. Thereafter, the prescribed amount of the insecticidal active ingredient and Yoshinox 424 of one-half of the amount of the said insecticidal active ingredient (by weight) were impregnated, as an acetone solution, onto the rod-form base to prepare a "rod" type formulation for fumigation to be tested.

A Petri dish, 14 cm in diameter and 7 cm in height, was coated with butter on the cylindrical inside wall, and 10 German cockroaches (5 males and 5 females) (*Blatella germanica*) per group were liberated in the Petri dish. Ten pieces of this Petri dish were placed for each test at the center of the bottom of a (70 cm)³ glass chamber. Thereafter, a small window leading to the inside of the chamber was opened, a stand having 0.7 g of each "rod" type formulation was placed in the chamber, and after firing it, the window was closed. Every time 10 and 20 minutes elapsed, five Petri dishes containing the cockroaches were taken out and placed in an observation room, and the number of knocked-down insects was counted with the lapse of time for 60 minutes. Then, the cockroaches were transferred to a clean container with water and diets, and after three days, the mortal and alive were observed.

The test results are as shown in Table 1.

TABLE 1

| Test compound and concentration (%) | Exposure time (min) | Knock-down ratio (%) | | | | | | Mortality (%) |
|---|---|---|---|---|---|---|---|---|
| | | 10' | 20' | 30' | 40' | 50' | 60' | |
| Compound (B) 6% | 10' | 0 | 36 | 64 | 78 | 92 | 98 | 76 |
| | 20' | — | 64 | 86 | 98 | 100 | 100 | 98 |
| Compound (B) 5% | 10' | 0 | 32 | 54 | 74 | 78 | 92 | 62 |
| | 20' | — | 62 | 82 | 96 | 100 | 100 | 90 |
| Compound (B) 4% | 10' | 0 | 26 | 48 | 64 | 72 | 82 | 56 |
| | 20' | — | 58 | 74 | 86 | 94 | 98 | 78 |
| Compound (A) 6% | 10' | 0 | 0 | 0 | 0 | 4 | 16 | 90 |
| | 20' | — | 0 | 0 | 6 | 22 | 38 | 100 |
| Compound (A) 2% | 10' | 0 | 0 | 0 | 0 | 0 | 0 | 66 |
| | 20' | — | 0 | 0 | 0 | 0 | 0 | 82 |
| Compound (A) 1% | 10' | 0 | 0 | 0 | 0 | 0 | 0 | 40 |
| | 20' | — | 0 | 0 | 0 | 0 | 0 | 62 |
| Compound (A) 5% + Compound (B) 1% | 10' | 0 | 7 | 12 | 26 | 44 | 52 | 94 |
| | 20' | — | 18 | 22 | 54 | 64 | 90 | 100 |
| Compound (A) 4% + Compound (B) 2% | 10' | 0 | 16 | 28 | 46 | 58 | 78 | 100 |
| | 20' | — | 20 | 32 | 54 | 60 | 88 | 100 |
| Compound (A) 3% + Compound (B) 3% | 10 | 0 | 38 | 48 | 78 | 92 | 98 | 96 |
| | 20' | — | 44 | 68 | 84 | 95 | 97 | 100 |
| Compound (A) 2% + Compound (B) 4% | 10' | 0 | 40 | 72 | 86 | 96 | 98 | 98 |
| | 20' | — | 66 | 88 | 94 | 98 | 100 | 100 |
| Compound (A) 1.5% + Compound (B) 4.5% | 10' | 0 | 38 | 68 | 83 | 94 | 98 | 92 |
| | 20' | — | 65 | 84 | 96 | 100 | 100 | 100 |
| Compound (A) 1% + Compound (B) 5% | 10' | 0 | 38 | 64 | 74 | 88 | 94 | 88 |
| | 20' | — | 60 | 78 | 90 | 100 | 100 | 98 |

From the results in Table 1, a synergistic effect due to combination is clearly noticed on comparing the effect of each single ingredient with that of the mixture thereof. That said synergistic effect is remarkable may be said more clearly from FIG. 1 in which the knock-down ratio after 10 minutes' exposure and 20 minutes' lapse subsequent thereto, and the mortality were each plotted against the mixing ratio.

It was found that the synergistic effect is noticed when the mixing ratio of compound (A) to compound (B) is in the range of 1:5 to 2:1, and that it is particularly remarkable when the mixing ratio is near to 1:2. Based on this result, the following Table 2 was made for the purpose of confirming the combination effect of a 2:1 mixture of the other pyrethroid type compound and the compound (A) as compared with the effect of the each compound constituting the mixture.

TABLE 2

| Test compound and concentration (%) | Exposure time (min) | Knock-down ratio (%) 10' | 20' | 30' | 40' | 50' | 60' | Mortality (%) |
|---|---|---|---|---|---|---|---|---|
| Compound (C) 4% + Compound (A) 2% | 10' | 26 | 52 | 70 | 94 | 99 | 100 | 100 |
|  | 20' | — | 80 | 98 | 100 | 100 | 100 | 100 |
| Compound (E) 4% + Compound (A) 2% | 10' | 0 | 24 | 47 | 50 | 74 | 92 | 98 |
|  | 20' | — | 50 | 64 | 70 | 96 | 100 | 100 |
| Compound (C) 6% | 10' | 10 | 48 | 64 | 88 | 96 | 100 | 84 |
|  | 20' | — | 74 | 92 | 100 | 100 | 100 | 100 |
| Compound (E) 6% | 10' | 0 | 14 | 28 | 46 | 58 | 78 | 68 |
|  | 20' | — | 48 | 62 | 70 | 82 | 95 | 88 |
| Compound (A) 6% | 10' | 0 | 0 | 0 | 0 | 4 | 16 | 90 |
|  | 20' | — | 0 | 0 | 4 | 22 | 36 | 100 |

From the result of Table 2, it can be confirmed that either of the mixtures of the present invention has a higher insecticidal effect than that of each of the compounds constituting said mixtures.

EXPERIMENTAL EXAMPLE 2

The compounds in Table 3 were dissolved in acetone so as to be combined as described in the table and impregnated into a porous ceramic plate [4 cm × 4 cm × 1.2 cm (thickness)] to prepare electro-heating type test mats.

The following test plots were prepared using Petri dishes, 14 cm in diameter and 7 cm in height, of which the inside wall was coated with butter for preventing insects from escape: (1) An open Petri dish test plot where a Petri dish is used as such; (2) an absorptive surface test plot which is a Petri dish having a filter paper at the bottom; and (3) a Petri dish (with cover) test plot which is a Petri dish covered at the top with a round filter paper having a rectangular opening of which the area corresponds to a one-fifth of the top area of the Petri dish.

Ten German cockroaches (5 males and 5 females) (*Blattella germanica*) were liberated in the each Petri dish.

Each test plot was arranged as shown in FIG. 2 in a Peet Grady's chamber (180 cm)$^3$. An electro-heating fumigant placed at the center of the chamber was heated electrically to about 300° C. for 15 minutes.

After 60 minutes' exposure, the test insects were transferred into a recovery container with water and diets, and after three days, the mortality was observed. The results are as shown in Table 3.

TABLE 3

| Test Compound | Dosage rate (mg/mat) | Mortality (%) Test plot (1) | (2) | (3) |
|---|---|---|---|---|
| Compound (A) | 200 | 100 | 100 | 100 |
|  | 100 | 100 | 64 | 98 |
|  | 50 | 88 | 44 | 76 |
| Compound (B) | 200 | 100 | 80 | 80 |
|  | 100 | 82 | 56 | 62 |
|  | 50 | 68 | 34 | 10 |
| Compound (C) | 100 | 100 | 82 | 90 |
| Compound (D) | 100 | 100 | 74 | 84 |
| Compound (E) | 100 | 72 | 38 | 16 |
| Compound (A) + Compound (B) | 50 / 50 | 100 | 100 | 92 |
| Compound (A) + Compound (B) | 30 / 70 | 100 | 100 | 100 |
| Compound (A) + | 30 |  |  |  |

TABLE 3-continued

| Test Compound | Dosage rate (mg/mat) | Mortality (%) Test plot (1) | (2) | (3) |
|---|---|---|---|---|
| Compound (C) | 70 |  |  |  |
| Compound (A) + | 30 | 100 | 100 | 100 |
| Compound (D) | 70 |  |  |  |
| Compound (A) + | 30 | 100 | 100 | 88 |
| Compound (E) | 70 |  |  |  |

From the result of tests on various conditions described in Table 3, it can be confirmed that either of the mixtures of the present invention has a higher insecticidal effect than that of each of the compounds constituting said mixtures.

EXPERIMENTAL EXAMPLE 3

An electro-heating type fumigating mat was prepared in the same manner as in Experimental Example 2. At the center of the bottom of a Petri dish, 20 cm in diameter and 5 cm in height, of which the inside wall was coated with butter for preventing insects from escape, was placed a triangular wooden shelter, 15 cm in height and 3 cm in side, in which ten German cockroaches (5 males and 5 females) (*Blattella germanica*) had previously acclimatized themselves. These Petri dishes were placed at the prescribed positions in a (180 cm)$^3$ Peet Grady's chamber as shown in FIG. 3.

The electro-heating type fumigating mat at the center of the chamber was heated in the same manner as in Experimental Example 2, and the number of the insects flushing out of the shelter and that of the knocked-down ones among them were counted at the lapse of time. From the each of numbers a flushing-out effect and a knock-down effect were obtained by the Finney's method, the former effect being expressed by a time required for 50% of the test insects to be flushed out ($FT_{50}$ value) and the latter effect being expressed by a time required for 50% of the test insects to be knocked down ($KT_{50}$ value). After 60 minutes' exposure, all the test insects were transferred into a recovery container with water and diets, and after three days, the mortality was obtained.

The results are shown in Table 4.

TABLE 4

| Test compound | Dosage rate (mg/mat) | $FT_{50}$ value (min) | $KT_{50}$ value (min) | Mortality (%) |
|---|---|---|---|---|
| Compound (A) | 200 | >60 | >60 | 12 |
|  | 100 | >60 | >60 | 0 |

TABLE 4-continued

| Test compound | Dosage rate (mg/mat) | $FT_{50}$ value (min) | $KT_{50}$ value (min) | Mortality (%) |
|---|---|---|---|---|
| | 50 | >60 | >60 | 0 |
| Compound (B) | 200 | 8 | 18 | 100 |
| | 100 | 15 | 23 | 86 |
| | 50 | 26 | 38 | 78 |
| Compound (C) | 100 | 12 | 20 | 98 |
| Compound (E) | 100 | 16 | 42 | 76 |
| Compound (A) + Compound (B) | 50 50 | 17 | 25 | 100 |
| Compound (A) + Compound (B) | 30 70 | 15 | 33 | 100 |
| Compound (A) + Compound (C) | 30 70 | 12 | 22 | 100 |
| Compound (A) + Compound (E) | 30 70 | 17 | 36 | 100 |

From Table 4, it is clearly noticed that an effective insect control can be attained by flushing out the insect lying in hiding, and also that either of the mixture of the present invention has a higher insecticidal effect than that of each of the compounds constituting said mixtures.

EXPERIMENTAL EXAMPLE 4

Direct spray test of aerosols, which were prepared in the manner of Formulation Example 3, was made for cockroaches by the test method as follows:

Ten German cockroaches were released into the container and then the container was put in a glass cylinder having a diameter of 20 cm and a height of 60 cm.

400 Mg±100 mg of each of test aerosol prepared in Formulation Example 3 was sprayed to the insects in the container and then the number of knocked-down cockroaches was counted at prescribed time intervals up to 20 minutes.

Then, the tested cockroaches were transferred into a fresh container with water and diets, and after three days, the motality was observed.

From relation between knock-down ratio and time, the $KT_{50}$ value (50% knock-down time) was calculated by Bliss's probit method.

The results obtained are shown in Table 5.

TABLE 5

| Test aerosol Active ingredient | ratio | $KT_{50}$ (min) | Kill (%) |
|---|---|---|---|
| Compound (A) + Compound (B) | 1.0 0.1 | 6.8 | 100 |
| Compound (A) + Compound (C) | 1.0 0.1 | 5.4 | 100 |
| Compound (A) + Compound (D) | 1.0 0.1 | 5.6 | 100 |
| Compound (A) + Compound (E) | 1.0 0.1 | 7.5 | 100 |
| Compound (A) + Compound (E) | 0.5 0.1 | 2.2 | 100 |
| Compound (A) + Compound (F) | 1.0 0.1 | 2.6 | 100 |
| Compound (A) + Compound (G) | 0.5 0.1 | 2.1 | 100 |
| Compound (A) + Compound (G) | 1.0 0.1 | 5.5 | 100 |
| Compound (A) + Compound (H) | 1.0 0.1 | 5.6 | 100 |
| Compound (A) + Compound (I) | 1.0 0.1 | 5.2 | 100 |
| Compound (A) + Compound (J) | 1.0 0.1 | 5.1 | 100 |
| Compound (A) + Compound (K) | 1.0 0.1 | 7.6 | 100 |
| Compound (A) + Compound (L) | 1.0 0.1 | 6.7 | 100 |
| Compound (A) + Compound (M) | 1.0 0.1 | 6.5 | 100 |
| Compound (A) + Compound (N) | 1.0 0.1 | | |
| Compound (A) | 1.0 | 9.1 | 100 |
| Compound (A) | 0.5 | 9.9 | 100 |
| Compound (B) | 0.1 | 7.2 | 100 |
| Compound (C) | 0.1 | 6.4 | 88 |
| Compound (D) | 0.1 | 6.6 | 80 |
| Compound (E) | 0.1 | 8.3 | 65 |
| Compound (F) | 0.1 | 3.5 | 13 |
| Compound (G) | 0.1 | 2.8 | 18 |
| Compound (H) | 0.1 | 6.5 | 13 |
| Compound (I) | 0.1 | 6.3 | 11 |
| Compound (J) | 0.1 | 5.9 | 17 |
| Compound (K) | 0.1 | 6.2 | 15 |
| Compound (L) | 0.1 | 8.8 | 54 |
| Compound (M) | 0.1 | 8.6 | 68 |
| Compound (N) | 0.1 | 7.5 | 70 |

What is claimed is:

1. An insecticidal composition comprising 3-(2-methoxy-phenyl)-5-methoxy-1,3,4-oxadizaol-2(3H)-one and a pyrethroid type compound represented by the formula, in a weight ratio of oxadiazol compound to pyrethroid compound being from 5:1 to 1:5.

2. The insecticidal composition according to claim 1, wherein the said composition contains 0.5 to 40% by weight of the active ingredient.

3. The insecticidal composition according to claim 1, wherein said composition is the insecticidal composition for fumigant, aerosol or oil liquid.

* * * * *